US009993283B2

(12) United States Patent
Ladtkow et al.

(10) Patent No.: US 9,993,283 B2
(45) Date of Patent: Jun. 12, 2018

(54) SELECTIVELY DEFORMABLE ABLATION DEVICE

(71) Applicant: COVIDIEN LP, Mansfield, MA (US)

(72) Inventors: Casey M. Ladtkow, Erie, CO (US); William O. Reid, Jr., Longmont, CO (US); Darion R. Peterson, Boulder, CO (US); Gene H. Arts, Berthoud, CO (US); John R. Vantuno, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 252 days.

(21) Appl. No.: 14/035,451

(22) Filed: Sep. 24, 2013

(65) Prior Publication Data

US 2014/0094799 A1 Apr. 3, 2014

Related U.S. Application Data

(60) Provisional application No. 61/708,861, filed on Oct. 2, 2012.

(51) Int. Cl.

*A61B 18/18* (2006.01)
*A61B 18/08* (2006.01)

(Continued)

(52) U.S. Cl.

CPC ........ *A61B 18/082* (2013.01); *A61B 18/1477* (2013.01); *A61B 2017/00314* (2013.01);

(Continued)

(58) Field of Classification Search

CPC .... A61B 2018/1475; A61B 2018/1465; A61B 18/1492; A61B 18/1477; A61B 18/082;

(Continued)

(56) References Cited

U.S. PATENT DOCUMENTS

D223,367 S 4/1972 Kountz
D263,020 S 2/1982 Rau, III (Continued)

FOREIGN PATENT DOCUMENTS

CN 1103807 6/1995
CN 1273519 A 11/2000

(Continued)

OTHER PUBLICATIONS

U.S. Appl. No. 13/835,183, filed Mar. 15, 2013, Arts.

(Continued)

*Primary Examiner* — Michael Peffley
*Assistant Examiner* — Amanda Zink

(57) ABSTRACT

In accordance with at least one aspect of this disclosure, an ablation apparatus includes a proximal body portion, a shaft extending distally from the proximal body portion, the shaft being selectively deformable utilizing at least one deformation system between a first position wherein the shaft is straight an a second position wherein the shaft is bent, the at least one deformation system configured to retain the shaft in each of the first and second positions, and at least one electrode disposed at least partially within the shaft, the electrode movable with the shaft upon movement of the shaft between the first and second positions.

20 Claims, 12 Drawing Sheets

340 320 350 305 302 310a 333 325

302 305 320 325 340 330 350 350 333 310a

(51) Int. Cl.
*A61B 18/14* (2006.01)
*A61B 18/00* (2006.01)
*A61B 17/00* (2006.01)

(52) U.S. Cl.
CPC ............... *A61B 2018/00023* (2013.01); *A61B 2018/00577* (2013.01); *A61B 2018/00791* (2013.01); *A61B 2018/1465* (2013.01)

(58) Field of Classification Search
CPC ........... A61B 2017/00314; A61B 2018/00023; A61B 2018/00577; A61B 2018/00791
USPC ......................................... 604/534, 535, 528
See application file for complete search history.

(56) References Cited

U.S. PATENT DOCUMENTS

D266,842 S 11/1982 Villers et al.
D278,306 S 4/1985 McIntosh
D295,893 S 5/1988 Sharkany et al.
D295,894 S 5/1988 Sharkany et al.
4,927,413 A 5/1990 Hess
D354,218 S 1/1995 Van de Peer
5,431,168 A 7/1995 Webster, Jr.
5,893,863 A 4/1999 Yoon
5,947,964 A * 9/1999 Eggers ................. A61B 5/0531 606/41
6,016,811 A 1/2000 Knopp et al.
D424,693 S 5/2000 Pruter
D424,694 S 5/2000 Tetzlaff et al.
D425,201 S 5/2000 Tetzlaff et al.
6,071,281 A 6/2000 Burnside et al.
6,073,051 A 6/2000 Sharkey et al.
6,106,521 A * 8/2000 Blewett ............. A61B 18/1477 600/105
6,146,379 A 11/2000 Fleischman et al.
6,251,128 B1 6/2001 Knopp et al.
D449,886 S 10/2001 Tetzlaff et al.
6,312,428 B1 * 11/2001 Eggers ................. A61B 5/0531 606/41
D457,958 S 5/2002 Dycus et al.
D457,959 S 5/2002 Tetzlaff et al.
6,451,014 B1 * 9/2002 Wakikaido ............. A61B 18/14 606/33
6,629,534 B1 * 10/2003 St. Goar ............ A61B 17/0469 128/898
D487,039 S 2/2004 Webster et al.
6,743,239 B1 6/2004 Kuehn et al.
D496,997 S 10/2004 Dycus et al.
D499,181 S 11/2004 Dycus et al.
7,041,095 B2 5/2006 Wang et al.
D525,361 S 7/2006 Hushka
D531,311 S 10/2006 Guerra et al.
D533,942 S 12/2006 Kerr et al.
7,147,633 B2 12/2006 Chee et al.
D535,027 S 1/2007 James et al.
7,197,349 B2 3/2007 Taimisto et al.
D541,418 S 4/2007 Schechter et al.
D541,938 S 5/2007 Kerr et al.
7,226,444 B1 6/2007 Ellman et al.
7,270,658 B2 9/2007 Woloszko et al.
D564,662 S 3/2008 Moses et al.
7,344,533 B2 3/2008 Pearson et al.
7,387,625 B2 6/2008 Hovda et al.
D576,932 S 9/2008 Strehler
7,419,487 B2 9/2008 Johnson et al.
D594,736 S 6/2009 Esjunin
D594,737 S 6/2009 Kelly et al.
D606,203 S 12/2009 Husheer et al.
7,678,108 B2 3/2010 Christian et al.
D613,412 S 4/2010 DeCarlo
D634,010 S 3/2011 DeCarlo
8,214,010 B2 7/2012 Courtney et al.
8,231,614 B2 7/2012 Dunning et al.
8,353,902 B2 * 1/2013 Prakash .......................... 606/33
8,398,587 B2 * 3/2013 Dewaele et al. ........... 604/95.04
D681,810 S 5/2013 DeCarlo
2002/0026145 A1 2/2002 Bagaoisan et al.
2003/0065373 A1 4/2003 Lovett et al.
2003/0088212 A1 5/2003 Tal
2003/0212394 A1 * 11/2003 Pearson ............. A61B 18/1477 606/41
2004/0153049 A1 8/2004 Hewitt et al.
2004/0236316 A1 11/2004 Danitz et al.
2006/0064085 A1 3/2006 Schechter et al.
2006/0106375 A1 5/2006 Werneth et al.
2006/0271031 A1 11/2006 Desinger et al.
2007/0049922 A1 3/2007 Rontal
2007/0083193 A1 4/2007 Werneth et al.
2007/0100424 A1 5/2007 Chew et al.
2007/0179496 A1 * 8/2007 Swoyer ............. A61B 18/1492 606/41
2007/0233044 A1 * 10/2007 Wallace et al. ............... 604/528
2008/0004615 A1 1/2008 Woloszko et al.
2008/0161890 A1 7/2008 Lafontaine
2008/0281293 A1 * 11/2008 Peh et al. ...................... 604/523
2009/0076499 A1 * 3/2009 Azure .................... A61B 18/14 606/41
2009/0209950 A1 8/2009 Starksen
2010/0004632 A1 1/2010 Wu et al.
2010/0125269 A1 5/2010 Emmons et al.
2010/0185161 A1 * 7/2010 Pellegrino .......... A61B 17/3472 604/272
2010/0211076 A1 * 8/2010 Germain ............ A61B 17/1642 606/84
2011/0009858 A1 * 1/2011 Ormsby et al. ................. 606/33
2011/0077498 A1 3/2011 McDaniel
2012/0053569 A1 3/2012 Honebrink et al.
2012/0330351 A1 12/2012 Friedman et al.
2013/0237980 A1 9/2013 Brannan
2013/0241769 A1 9/2013 Brannan et al.
2013/0245624 A1 9/2013 Bahney
2013/0253500 A1 9/2013 Lee et al.
2013/0261617 A1 10/2013 Podhajsky
2013/0261620 A1 10/2013 Brannan et al.
2013/0267946 A1 10/2013 Brannan et al.
2013/0289560 A1 10/2013 DeCarlo et al.
2013/0296841 A1 11/2013 Brannan
2013/0304056 A1 11/2013 Prakash et al.
2013/0304057 A1 11/2013 Rossetto
2013/0317407 A1 11/2013 Reid, Jr. et al.
2013/0317495 A1 11/2013 Brannan
2013/0317499 A1 11/2013 Brannan et al.
2013/0324910 A1 12/2013 Ohri et al.
2013/0324911 A1 12/2013 Ohri et al.
2013/0338661 A1 12/2013 Behnke, II
2014/0005655 A1 1/2014 Brannan
2014/0243642 A1 * 8/2014 Deac .................. A61B 5/04085 600/374
2015/0066016 A1 * 3/2015 Miles ................. A61B 18/1492 606/34
2015/0094712 A1 * 4/2015 Murdeshwar ...... A61B 17/3415 606/39
2016/0367314 A1 * 12/2016 Dougherty ......... A61B 18/1482

FOREIGN PATENT DOCUMENTS

DE 390937 3/1924
DE 1099658 2/1961
DE 1139927 11/1962
DE 1149832 6/1963
DE 1439302 1/1969
DE 2439587 2/1975
DE 2455174 5/1975
DE 2407559 8/1975
DE 2415263 10/1975
DE 2429021 1/1976
DE 2460481 6/1976
DE 2602517 7/1976
DE 2504280 8/1976
DE 2627679 1/1977
DE 2540968 3/1977

(56) References Cited

FOREIGN PATENT DOCUMENTS

| | | | |
|---|---|---|---|
| DE | 2820908 | | 11/1978 |
| DE | 2803275 | | 8/1979 |
| DE | 2823291 | | 11/1979 |
| DE | 2946728 | | 5/1981 |
| DE | 3143421 | | 5/1982 |
| DE | 3045996 | | 7/1982 |
| DE | 3120102 | | 12/1982 |
| DE | 3510586 | | 10/1986 |
| DE | 3604823 | | 8/1987 |
| DE | 8712328 | | 3/1988 |
| DE | 3711511 | | 6/1988 |
| DE | 90 06 694 | U1 | 8/1990 |
| DE | 3904558 | | 8/1990 |
| DE | 3942998 | | 7/1991 |
| DE | 4238263 | | 5/1993 |
| DE | 4303882 | | 8/1994 |
| DE | 4339049 | | 5/1995 |
| DE | 29616210 | | 1/1997 |
| DE | 19608716 | | 4/1997 |
| DE | 19751106 | | 5/1998 |
| DE | 19717411 | | 11/1998 |
| DE | 19751108 | | 5/1999 |
| DE | 19801173 | | 7/1999 |
| DE | 19848540 | | 5/2000 |
| DE | 10224154 | | 12/2003 |
| DE | 10310765 | | 9/2004 |
| DE | 10328514 | | 3/2005 |
| DE | 102004022206 | | 12/2005 |
| DE | 202005015147 | | 3/2006 |
| DE | 102009015699 | | 5/2010 |
| EP | 0 246 350 | | 11/1987 |
| EP | 0 521 264 | | 1/1993 |
| EP | 0 556 705 | | 8/1993 |
| EP | 0 558 429 | | 9/1993 |
| EP | 0 836 868 | | 4/1998 |
| EP | 0 882 955 | | 12/1998 |
| EP | 1013228 | A1 | 6/2000 |
| EP | 1 050 279 | | 11/2000 |
| EP | 1 159 926 | | 5/2001 |
| EP | 0 648 515 | | 4/2003 |
| EP | 1 870 052 | A2 | 12/2007 |
| EP | 2 322 111 | A1 | 5/2011 |
| EP | 2338434 | A2 | 6/2011 |
| FR | 179 607 | | 11/1906 |
| FR | 1 275 415 | | 10/1961 |
| FR | 1 347 865 | | 11/1963 |
| FR | 2 235 669 | | 1/1975 |
| FR | 2 276 027 | | 1/1976 |
| FR | 2 313 708 | | 12/1976 |
| FR | 2 502 935 | | 10/1982 |
| FR | 2 517 953 | | 6/1983 |
| FR | 2 573 301 | | 5/1986 |
| FR | 2 862 813 | | 5/2005 |
| FR | 2 864 439 | | 7/2005 |
| JP | 5-5106 | | 1/1993 |
| JP | 05-40112 | | 2/1993 |
| JP | 06343644 | | 12/1994 |
| JP | 07265328 | | 10/1995 |
| JP | 08056955 | | 3/1996 |
| JP | 08252263 | | 10/1996 |
| JP | 09000492 | | 1/1997 |
| JP | 09010223 | | 1/1997 |
| JP | 11244298 | | 9/1999 |
| JP | 2000342599 | | 12/2000 |
| JP | 2000350732 | | 12/2000 |
| JP | 2001003776 | | 1/2001 |
| JP | 2001008944 | | 1/2001 |
| JP | 2001029356 | | 2/2001 |
| JP | 2001037775 | | 2/2001 |
| JP | 2001128990 | | 5/2001 |
| JP | 2001231870 | | 8/2001 |
| JP | 2005261521 | A | 9/2005 |
| JP | 2008142467 | | 6/2008 |
| JP | 2010012145 | A | 1/2010 |
| JP | 201198211 | A | 5/2011 |
| KR | 20070093068 | | 9/2007 |
| KR | 20100014406 | | 2/2010 |
| KR | 20120055063 | | 5/2012 |
| SU | 166452 | | 11/1964 |
| SU | 401367 | | 11/1974 |
| SU | 727201 | | 4/1980 |
| WO | WO00/36985 | | 6/2000 |
| WO | WO02/078777 | | 10/2002 |
| WO | 2006021095 | A1 | 3/2006 |
| WO | WO2010/035831 | | 4/2010 |
| WO | 2011085212 | A2 | 7/2011 |
| WO | WO01/95810 | | 12/2011 |

OTHER PUBLICATIONS

U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.

(56) References Cited

OTHER PUBLICATIONS

C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part 1", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.

(56) References Cited

OTHER PUBLICATIONS

Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. 1, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology , "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
International Search Report No. PCT/US2013/061612 dated Jan. 20, 2014.
Extended European Search Report for 13844185.2 dated Sep. 9, 2016.
Chinese Office Action for application No. 2013800352018 dated Jul. 19, 2016.
Supplementary Partial European Search Report for EP 13 84 4185 dated May 17, 2016.
Chinese Office Action for application No. 201380035203.8 dated Apr. 28, 2017.
Japanese Office Action dated Jun. 20, 2017 issued in corresponding JP Application No. 2015-534619.
Japanese Office Action dated Mar. 2, 2018 issued in corresponding JP Application No. 2015-534619.

* cited by examiner

SELECTIVELY DEFORMABLE ABLATION DEVICE

CROSS REFERENCE TO RELATED APPLICATION

The present application claims the benefit of and priority to U.S. Provisional Application Ser. No. 61/708,861, filed on Oct. 2, 2012, the entire contents of which are incorporated herein by reference.

BACKGROUND

1. Technical Field

The present disclosure relates to medical instruments. More particularly, the present disclosure is directed to selectively deformable medical devices for use in a surgical procedure.

2. Background of the Related Art

The use of radio-frequency (RF) and other forms of energy to create therapeutic lesions in living bodies to facilitate healing has been around for many decades. Ablation electrodes, for example, are configured to be inserted into a living body and to apply energy to surrounding tissue to form these tissue lesions. A typical ablation electrode incorporates an insulated sheath from which an exposed (uninsulated) tip extends that emits energy to surrounding tissue to create a tissue lesion.

Generally, the ablation electrode is coupled between a grounded RF power source, e.g., an electrosurgical generator, and a reference ground or indifferent electrode, e.g., return electrode pad, that is in contact with and dimensioned to engage a large surface of the body. When an RF voltage is provided between the ablation electrode and the reference ground, RF current flows from the ablation electrode through the body and back to the energy source via the return electrode pad. Typically, the current density is very high near the tip of the ablation electrode, which heats and destroys the adjacent tissue.

Many surgical instruments incorporate deformable or bendable shafts that allow the instrument to be better positioned within an internal surgical site. For example, U.S. Pat. No. 6,911,029 to Platt, the entire disclosure of which is hereby incorporated by reference herein, discloses an electrosurgical coagulator including an articulatable member. With respect to ablation devices, providing a deformation system that allows for bending or deformation would facilitate the insertion and/or placement of the electrode within a living body adjacent the target tissue to be treated.

SUMMARY

As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

In accordance with at least one aspect of this disclosure, an ablation apparatus includes a proximal body portion, a shaft extending distally from the proximal body portion, the shaft being selectively deformable utilizing at least one deformation system between a first position wherein the shaft is straight and a second position wherein the shaft is bent, the at least one deformation system configured to retain the shaft in each of the first and second positions, and at least one electrode disposed at least partially within the shaft, the electrode movable with the shaft upon movement of the shaft between the first and second positions.

In accordance with another aspect of this disclosure the deformation system comprises a goose-neck type shaft having at least two links operably coupled to each other.

In accordance with yet another aspect of this disclosure, the goose-neck type shaft includes a flexible layer disposed thereon to cover one or more separations between the at least two links.

In accordance with still yet another aspect of this disclosure, the shaft is made of a flexible material, and the deformation system comprises a line pull system, the line pull system comprising at least one anchor fixedly attached to the shaft, and at least one line connected to the at least one anchor and configured to be pulled to bend the shaft.

In accordance with still yet another aspect of this disclosure, the at least one line pull system comprises a first anchor connected to a first line, a second anchor connected to a second line and a third anchor connected to a third line, each anchor being spaced about equal distances circumferentially around the shaft such that the shaft is bendable in any desired direction.

In accordance with still yet another aspect of this disclosure, the shaft further comprises a flexible material and the deformation system comprises at least one of a material selected from the group consisting of a magnet and a ferromagnetic material, the material allowing the shaft to be moved by a magnetic field in the direction of the magnetic field.

In accordance with still yet another aspect of this disclosure, the deformation system further includes the material disposed within the flexible material at the distal end of the shaft.

In accordance with still yet another aspect of this disclosure wherein the deformation system comprises a weave having a rigid state and a deformable state.

In accordance with still yet another aspect of this disclosure, the rigid state is an elongated state and the deformable state is a neutral state.

In accordance with still yet another aspect of this disclosure, the deformable state is an elongated state and the rigid state is a neutral state.

In accordance with still yet another aspect of this disclosure, the deformation system comprises at least one semi-rigid rod configured to bend and hold the bent position.

In accordance with still yet another aspect of this disclosure, the semi-rigid rod is made of at least one metal.

In accordance with still yet another aspect of this disclosure, the deformation system includes at least one reservoir disposed within the shaft and at least one fluid supply connected to the reservoir to act as a pressure source, wherein the shaft is bendable when the reservoir is depressurized and rigid when the reservoir is pressurized.

In accordance with still yet another aspect of this disclosure, the deformation system comprises an electro-rheological material selectively connected to an electrical supply, the electro-rheological material having a rigid state and a deformable state.

In accordance with still yet another aspect of this disclosure, the electro-rheological material is in the deformable state when subjected to an electrical current.

In accordance with still yet another aspect of this disclosure, the electro-rheological material is in the rigid state when subjected to an electrical current.

In accordance with still yet another aspect of this disclosure, the deformation system comprises a magneto-rheological material selectively subjected to a magnetic field, the magneto-rheological material having a rigid state and a deformable state.

In accordance with still yet another aspect of this disclosure, wherein the magneto-rheological material is in the rigid state when subjected to a magnetic field.

In accordance with still yet another aspect of this disclosure, the deformation system comprises a spring winding disposed on said shaft, wherein the spring winding is connected to a tightener such that spring winding may be tightened to become substantially rigid and loosened to become deformable.

In accordance with still yet another aspect of this disclosure, a method for ablating a target site comprises providing an ablation apparatus including a proximal body portion, a shaft extending distally from the proximal body portion, the shaft being selectively deformable utilizing at least one deformation system between a first position wherein the shaft is straight and a second position wherein the shaft is bent, the at least one defamation system configured to retain the shaft in each of the first and second positions, and at least one electrode disposed at least partially within the shaft and extending from a distal end of the shaft, the electrode movable with the shaft upon movement of the shaft between the first and second positions, inserting the shaft into an incision, bending the shaft to position the at least one electrode at a target location and retaining the shaft in the bent position, and ablating the target location.

BRIEF DESCRIPTION OF THE DRAWINGS

The above and other aspects, features, and advantages of the present disclosure are described in detail with reference to the accompanying drawings, wherein like reference numerals may refer to similar or identical elements.

DETAILED DESCRIPTION

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
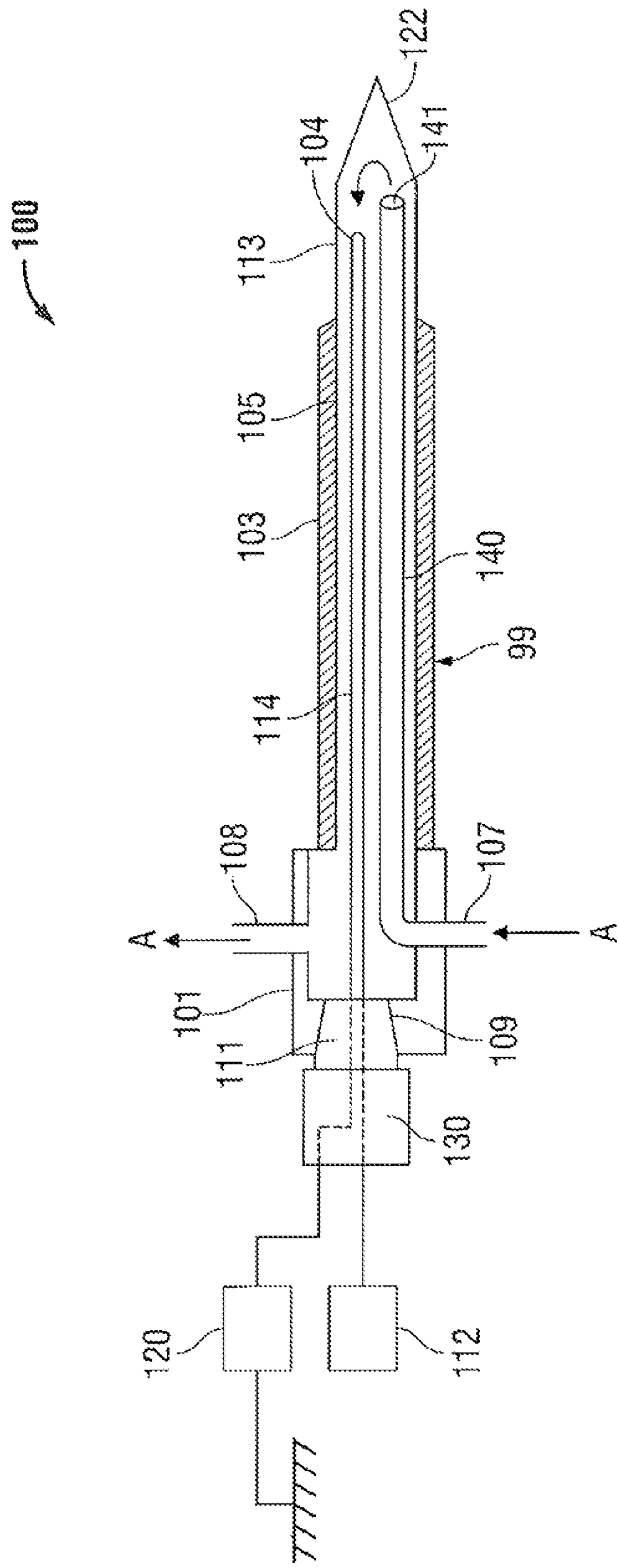
FIG. 1 is a schematic, side, cross-sectional view of an ablation apparatus provided in accordance with the present disclosure.
Figure 2A:
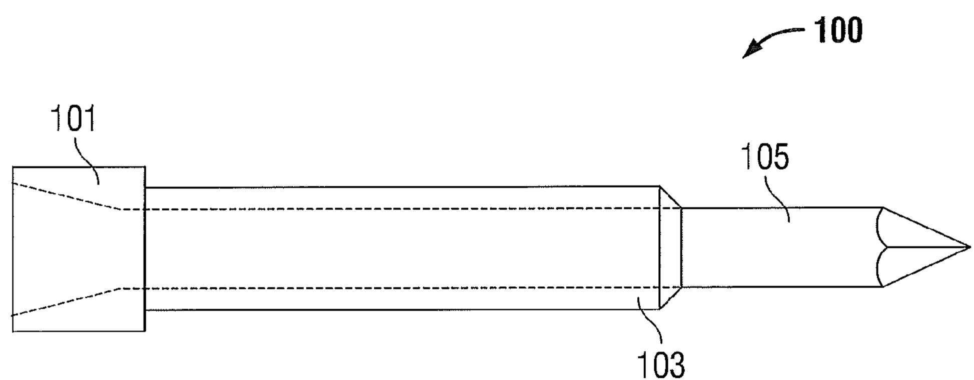
FIG. 2A is a side view of an ablation apparatus provided in accordance with the present disclosure in a straight position.
Figure 2B:
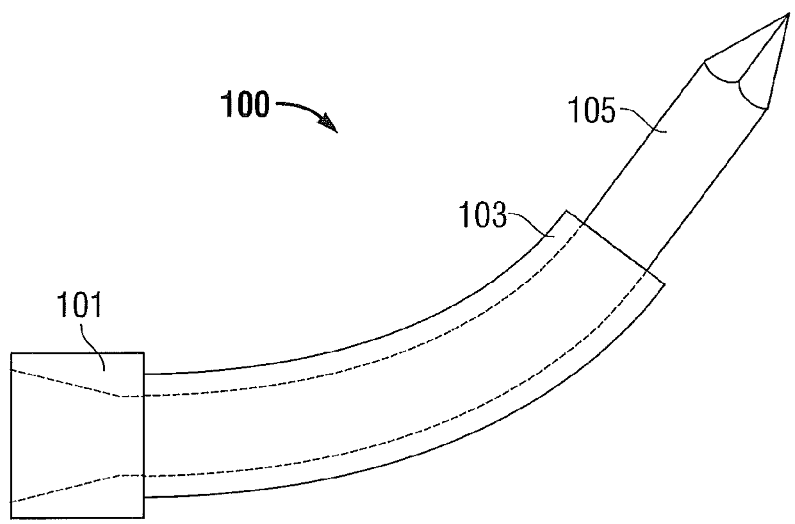
FIG. 2B is a side view of the ablation apparatus of FIG. 2A in a bent or deformed position.
Figure 3A:
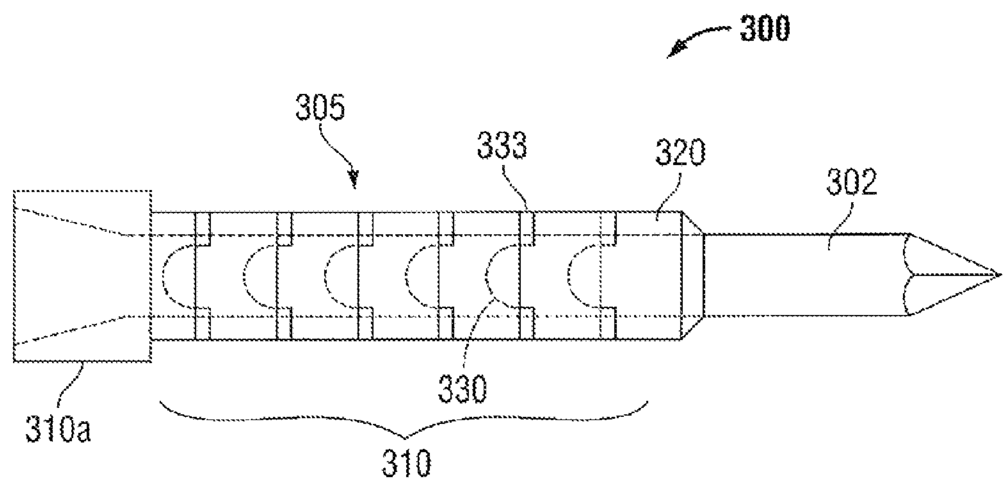
FIG. 3A is a side view of another ablation apparatus provided in accordance with the present disclosure including a series of links disposed in a straight position.
Figure 3B:
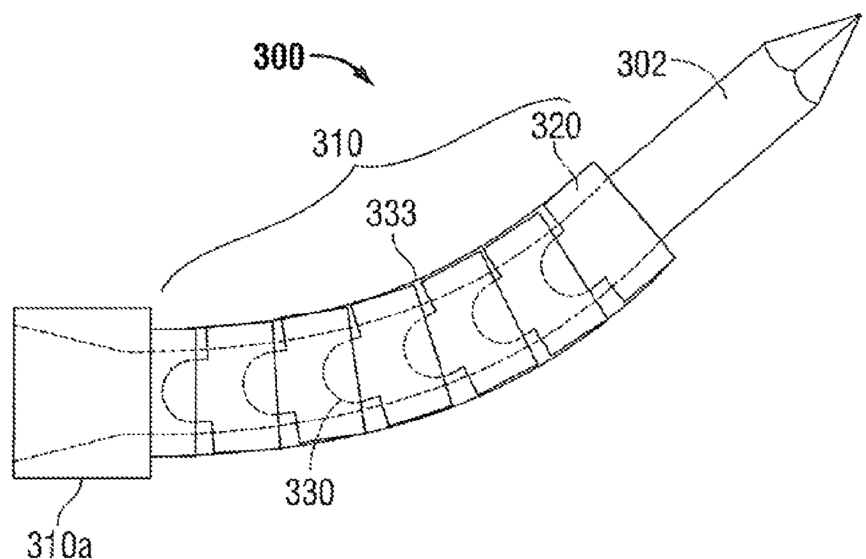
FIG. 3B is a side view of the ablation apparatus of FIG. 3A in a bent position.
Figure 4A:
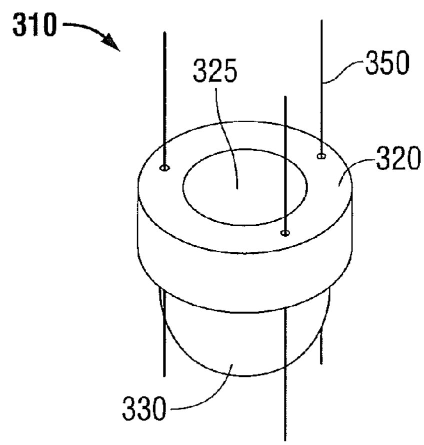
FIG. 4A is a top, perspective view of a representative link of the ablation apparatus of FIGS. 3A and 3B.
Figure 4B:
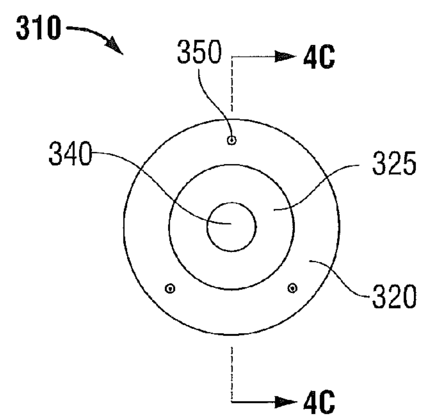
FIG. 4B is a front view of the link of FIG. 4A.
Figure 4C:
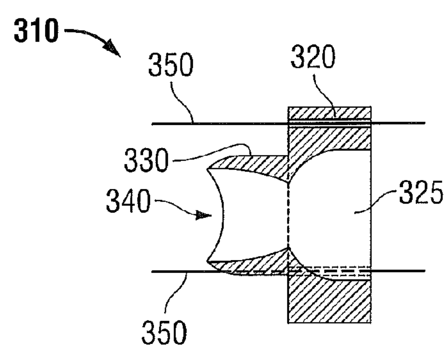
FIG. 4C is a side, cross-sectional view of the link of FIG. 4B taken along section line 4C-4C.

Referring to FIGS. 1, 2A and 2B, an embodiment of an ablation device, e.g., radiofrequency ablation apparatus 100, is shown including an elongated electrode 105 configured for insertion into tissue, either percutaneously or intraoperatively, e.g., into an open wound site. The electrode 105 includes a closed, pointed tip 122 that facilitates penetration through tissue, although other configurations are also contemplated.

The electrode 105 is at least partially disposed within shaft 103, which includes one or more insulative coatings or sleeves extending over at least a portion of the electrode 105. A distal end 113 of the electrode 105 extends distally from the shaft 103 such that the distal end 113 including the pointed tip 122 is exposed. The exposed distal end 113, when in contact with target tissue within the body and when energized with a high frequency current functions to heat tissue in the surrounding volume near the exposed distal end 113. Although the electrode 105 is shown and described herein as an RF electrode for radio frequency ablation, electrode 105 may alternatively be configured as a microwave antenna for microwave ablation, or any other suitable energy delivery device.

The electrode 105 is formed at least partially from a flexible material and/or includes flexible couplings, e.g., flexible conductive joints or linkages, such that, as will be described in greater detail below with respect to the various deformation systems provided herein, electrode 105 may be shaped to a desired configuration upon selective deformation of shaft 103. Alternatively, the deformation system may be coupled to or incorporated in electrode 105. In such embodiments, shaft 103 may be formed from a flexible material and/or may include flexible couplings such that shaft 103 is shaped in accordance with the selective deformation of electrode 105.

The ablation apparatus 100 further includes a proximal body portion 101 that includes respective inlet and outlet tubes 107 and 108. Coolant fluid is injected or urged under pressure into inlet tube 107 and through internal tube 140 so as to emanate from lumen 141 of internal tube 140 in proximity to the exposed distal end 113 of the electrode 105. The coolant fluid then circulates back through the electrode 105, as indicated by arrow “A,” ultimately exiting electrode 105 via the outlet tube 108 in the proximal body portion 101, although it is also contemplated that the direction of fluid flow be reversed. In either configuration, a so-called “cooled tip” electrode system is provided to maintain the distal end 113 of the electrode 105 in a relatively cooled state during use. Other coolant systems may also be employed with the ablation apparatus 100.

Continuing with reference to FIGS. 1, 2A and 2B, the proximal body portion 101 includes a luer-type female connector 109, although other connectors are contemplated. A high frequency or thermo-sensing probe 130 is inserted and sealed within the female connector 109 via a corresponding male luer connector 111. The probe 130 includes a probe shaft 114 which extends distally through the electrode 105. A distal end 104 of probe 130 includes a thermal sensor (not shown) configured to sense the temperature of the coolant fluid at the exposed distal end 113 of the electrode 105. Since the exposed distal end 113 is contiguous and in contact with the target tissue within the patient’s body, the thermal sensor (not shown) at distal end 104 of thermo probe 130 provides an indication of the temperature of tissue immediately outside of the exposed distal end 113. Thermo probe 130 may be electrically coupled to generator 120 and/or a thermal-sensing circuit 112. The generator 120, as mentioned above, is the source of high frequency voltage which produces the high frequency current that emanates from the electrode 105. The thermal-sensing circuit 112 may be a thermocouple type, and the thermal probe 130 may be a bi-metal junction thermocouple such as copper constantan, although any other suitable probe 130 and thermal-sensing circuit 112 may be provided.

The shaft 103 of ablation device 100 is selectively deformable utilizing one or more of the deformation systems described hereinbelow to allow the shaft 103 and electrode 105 to bend as shown in the figures that follow. More specifically, shaft 103 may be bent from a first configuration, e.g., a straight configuration (see FIG. 2A), to a second configuration, e.g., a bent configuration (see FIG. 2B) to likewise bend electrode 105 to position distal end 113 of electrode 105 adjacent target tissue to be treated. Various deformation systems and the like configured for use with ablation apparatus 100 are described below.

Referring to FIGS. 3A-5B, deformation system 300 includes a goose-neck type shaft 305 having two or more links 310 operably coupled to each other. Each link 310 includes a flange 320 with a socket 325 defined therein for receiving a hinge portion 330 of an adjacent link 310. The links 310 cooperate to define an elongated opening 340 that is configured to receive an electrode 302 (similar to the electrode 105) therethrough. The flange 320 may be of any desired operable shape for accepting the hinge portion 330 and allowing the hinge portion 330 to operably move. For example, as shown in FIGS. 3A-5B, the socket 325 is substantially spherical-shaped to accept a substantially spherical-shaped hinge portion 330. The goose-neck type shaft 305 further includes an outer flexible layer 333 disposed thereabout to cover the separations between the links 310 (see FIG. 3B). The outer flexible layer 333 may be disposed on the outer periphery of shaft 305 or may fully encase links 310 of shaft 305.

The electrode 302 extends through the opening 340 defined by links 310. More specifically, similarly as mentioned above with respect to electrode 105 (FIG. 1), electrode 302 may be formed at least partially from a flexible material or may include flexible couplings, e.g., flexible conductive joints, such that, as the shaft 305 is articulated or bent to a desired orientation, the electrode 302 bends in a similar manner. The electrode 302 may further be configured to slide relative to and within the shaft 305 upon movement of shaft 305 to one or more orientations.

Figure 5A:
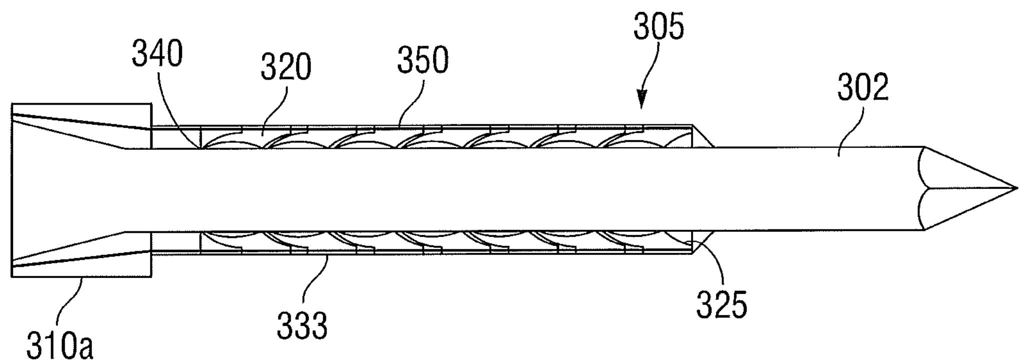
FIG. 5A is an internal, side view of the ablation apparatus of FIGS. 3A and 3B oriented in a straight position.
Figure 5B:
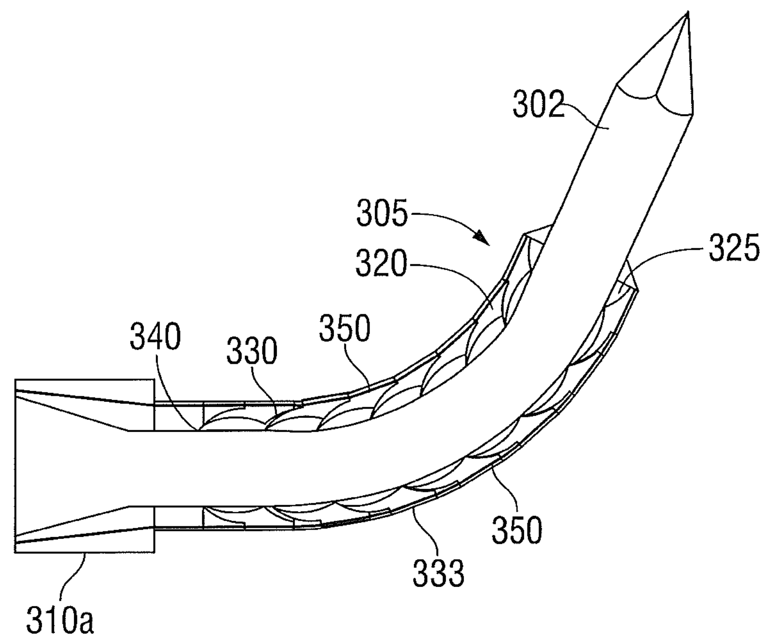
FIG. 5B is an internal, side view of the ablation apparatus of FIGS. 3A and 3B oriented in a bent position.

Referring more specifically to FIGS. 5A and 5B, shaft 305 is shown in a first straight position (FIG. 5A) and a second bent position (FIG. 5B), respectively. While the degree of directional change between adjacent links 310 is limited by the inherent design of each link 310, a successive series of links 310 will allow any desired degree of bending as each individual link 310 compounds the overall flexation of the shaft 305.

The goose-neck type shaft 305 may also include a locking feature such that after the goose-neck type shaft 305 is bent and positioned as desired, a locking mechanism may be set to prevent further bending. In one embodiment, the locking mechanism includes a system of wires 350 that are positionable to compress and lock each link 310 against a subsequent link creating a resulting force that holds a desired shaft shape. For example, if each wire 350 is fixed to an anchor link 310*a* and extends through each of the other links 310, the wires 350 may be pulled such that each link 310 becomes forcibly immobile against an adjacent link 310 as a result of the compressive force applied therethrough. Further, the compression may allow the links 310 to collapse into each other reducing gaps between the flange portions 320, thus not allowing any relative motion to occur between the links 310.

Figure 6A:
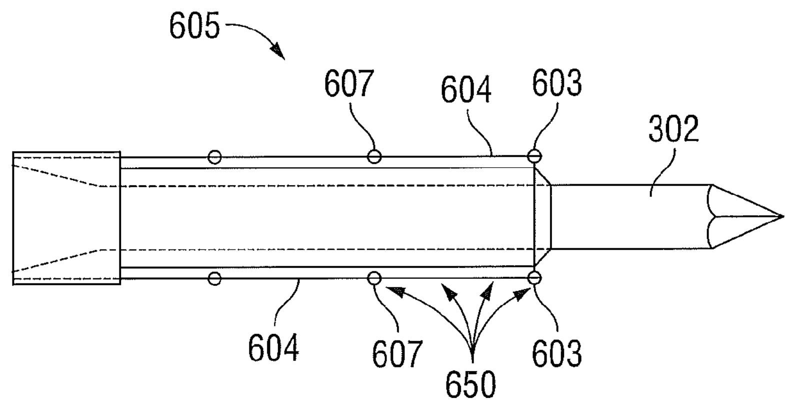
FIG. 6A is a schematic illustration of another ablation apparatus provided in accordance with the present disclosure in a straight position.
Figure 6B:
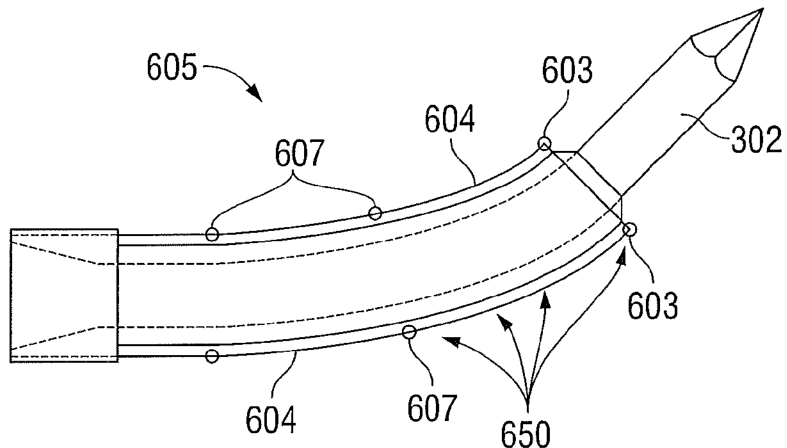
FIG. 6B is a schematic illustration of the ablation apparatus of FIG. 6A in a bent position.
Figure 6C:
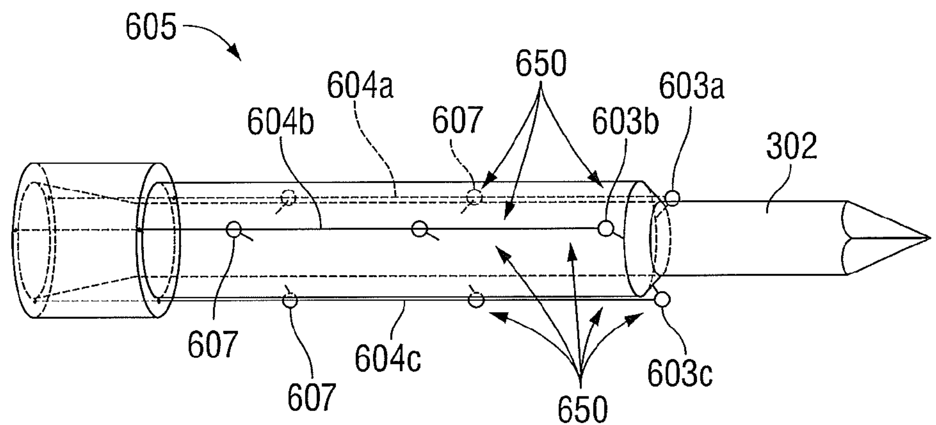
FIG. 6C is a perspective view of another ablation apparatus provided in accordance with the present disclosure in a straight position.

Referring to FIGS. 6A-6C, another embodiment of a deformation system is shown including a shaft 605 made of a flexible material, and having a line pull system 650. Line pull system 650 includes at least one line 604 connected to at least one anchor 603 attached at the distal end of the shaft 605. The line pull system 650 is pulled manually to bend the shaft 605 to a desired orientation. The flexible material forming shaft 605 may include any suitable plastic, foam, rubber, polymer, weave, malleable metal, or any combination thereof as desired. The flexible material may also be biocompatible. The line pull system 650 may include additional lines 604 connected to a second anchor 603. The line pull system 650 may further include a slider 607 that the one or more lines 604 moveably pass through such that the at least one line 604 may be kept to the contour of the shaft 605 as it bends under tension of the at least one line 604.

As shown in FIG. 6C, the line pull system 650 may further include a first anchor 603*a* connected to a first line 604*a*, a second anchor 603*b* connected to a second line 604*b* and a third anchor 603*c* connected to a third line 604*c*, each anchor being spaced about equal distances circumferentially around the shaft 605 such that a bend in any direction may be effected. More specifically, at least one line 604 of the line pull system 650 may be pulled to effectuate a bend in a desired direction. By pulling multiple lines 604, a bend in any desired direction may be effected due to the resulting forces applied by the pulled lines 604 to each respective anchor 603 on the shaft 605. This ability to bend the shaft 605 in multiple directions not only facilitates positioning of the instrument, but also allows the clinician to treat a plurality of target sites without having to rotate the entire instrument.

Figure 7A:
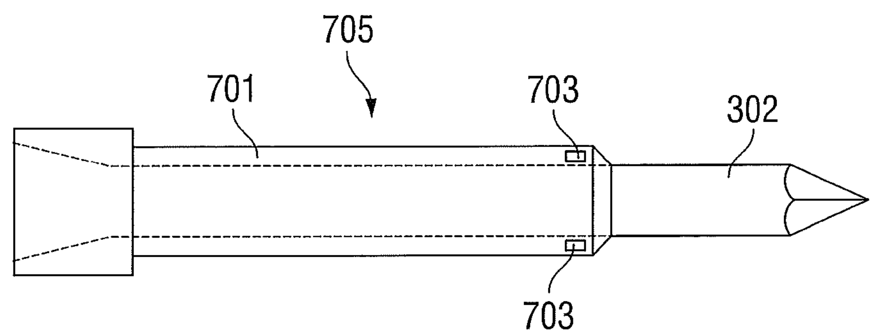
FIG. 7A is a schematic illustration of another ablation apparatus provided in accordance with the present disclosure in a straight position.
Figure 7B:
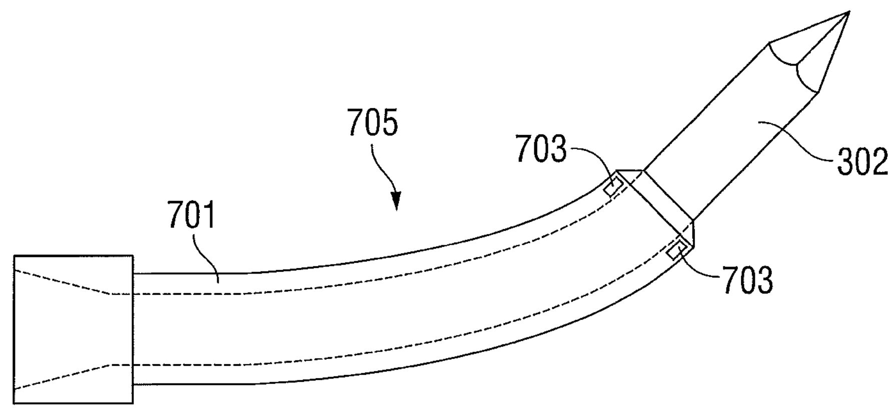
FIG. 7B is a schematic illustration of the ablation apparatus of FIG. 7A in a bent position.
Figure 7C:
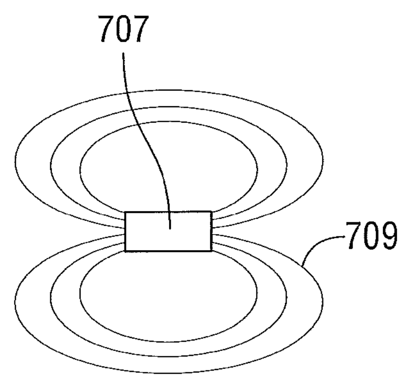
FIG. 7C is an illustration of a magnet emitting a magnetic field.

Referring to FIGS. 7A-7C, another embodiment of a shaft 705 is formed at least partially from a flexible material, similar to the flexible materials described above, and includes deformation system having at least one ferromagnetic material 703 disposed on or within the shaft 705 that allows the shaft 705 to be pulled or pushed by a magnetic field 709 created by a magnet 707. The magnet 707, as shown in FIG. 7C, may be a permanent magnet or an electro-magnet, and may be separate from the shaft 705, or may be disposed anywhere along or within the shaft 705 or proximal body portion 701. The at least one ferromagnetic material 703 may be incorporated into the shaft 705 itself, or may otherwise be coupled to the shaft 705 in any suitable fashion. In particular, the ferromagnetic material 703 may be disposed towards the distal end of the shaft 705 to facilitate accurate placement of the electrode 302.

The deformation system, as shown in FIGS. 7A and 7B, allows a clinician to bend the shaft 705 to a desired position by applying a magnetic field in the vicinity of the ferromagnetic material 703. The bend may be controlled as a function of field intensity and distance to the source of the magnetic field. Thus, the more powerful the magnetic field and/or the closer the shaft 705 is to the source of the magnetic field, the more the shaft 705 bends.

Figure 8A:
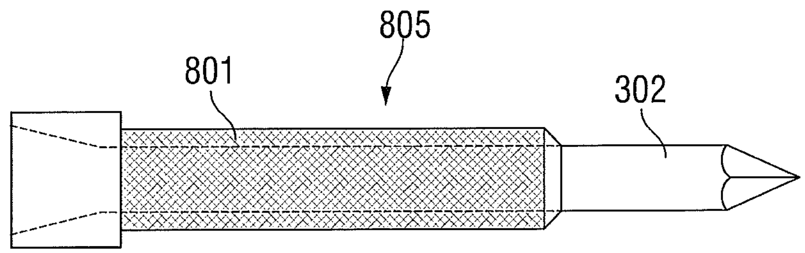
FIG. 8A is a side view of another ablation apparatus provided in accordance with the present disclosure in a straight but flexible position.
Figure 8B:
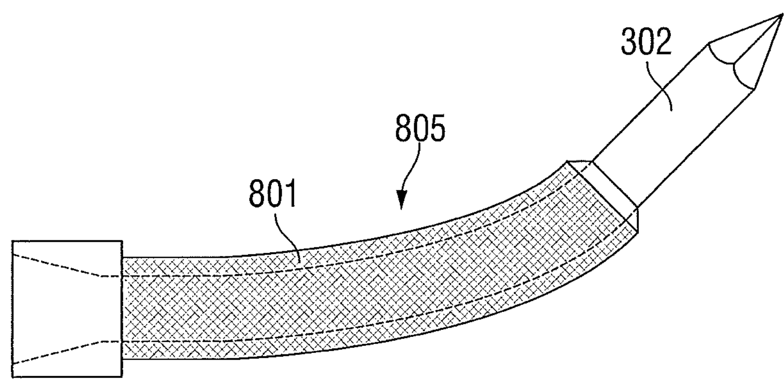
FIG. 8B is a side view of the ablation apparatus of FIG. 8A in a bent position.
Figure 8C:
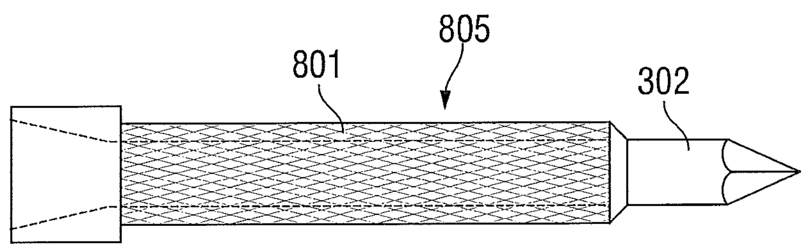
FIG. 8C is a side view of another ablation apparatus provided in accordance with the present disclosure in a straight and rigid position.

Referring to FIGS. 8A-8C, another embodiment of a deformation system includes a weave 801 disposed on or within the shaft 805 having a rigid state and a deformable state. For example, the rigid state may be an elongated state and the deformable state is a neutral or compressed state, such that when the weave 801 is pulled or extended, the weave 801 locks up and prevents bending of the shaft 805. In other embodiments, the deformable state is an elongated state and the rigid state is a neutral or compressed state such that compressing the weave 801 locks up the weave 801 and prevents bending of the shaft 805.

By using such a deformation system, as shown in FIGS. 8A-8C, a clinician may bend the shaft 805 to a desired position when the weave 801 is deformable. For example, the clinician may compress the weave 801 (see FIGS. 8A and 8B) and proceed to bend or deform the shaft 805. When the clinician is satisfied with the shape, the clinician may then pull the weave 801 to make it rigid (see FIG. 8C).

Figure 9A:
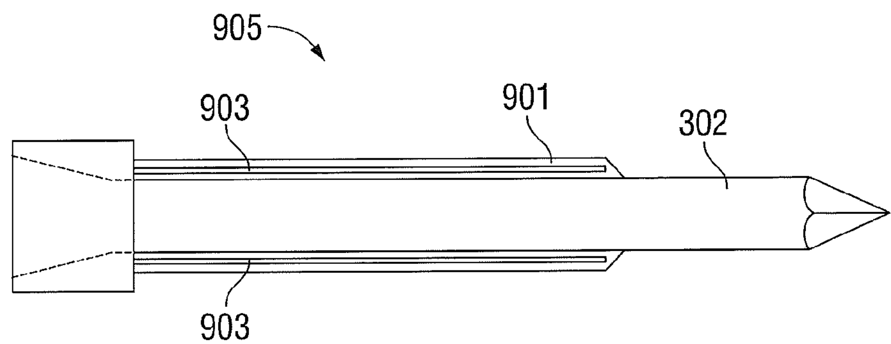
FIG. 9A is a side cross-sectional view of another ablation apparatus provided in accordance with the present disclosure in a straight position.
Figure 9B:
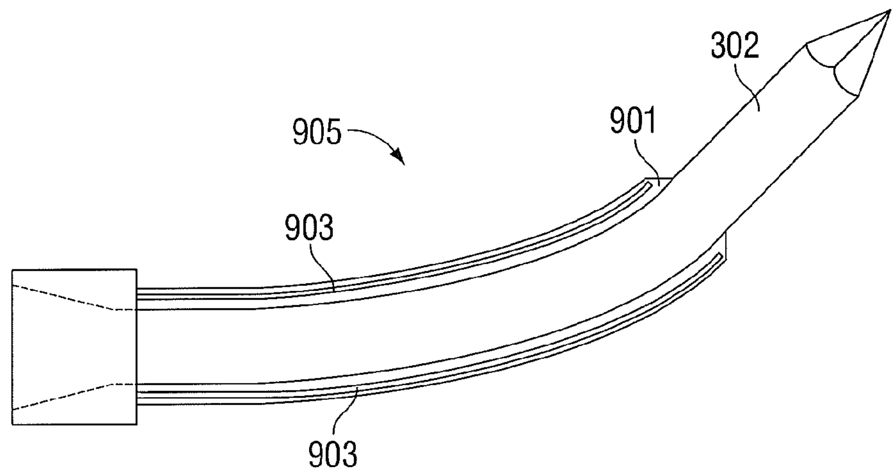
FIG. 9B is a side cross-sectional view of the ablation apparatus of FIG. 9A in a bent position.

Referring to FIGS. 9A and 9B, deformation system includes at least one semi-rigid rod 903 disposed on or within the at least one shaft 905. The shaft 905 is formed at least partially from a flexible material, similarly as described above. The semi-rigid rod 903 is configured to bend and hold its bent position. The at least one semi-rigid rod 903 may be made at least partially of metal or another suitable material. The at least one semi-rigid rod 903 allows the shaft 905 to be bent and to hold the bent shape because the bent semi-rigid rod 903 will not allow the flexible material 901 to bend back under its normal restoring force. As such, a clinician may mechanically deform the shaft 905 to a desired position and it will hold shape due to the semi-rigid rod 903 having a larger resistance to restoration than the restoring force of the flexible material 901 and any other static forces.

Figure 10A:
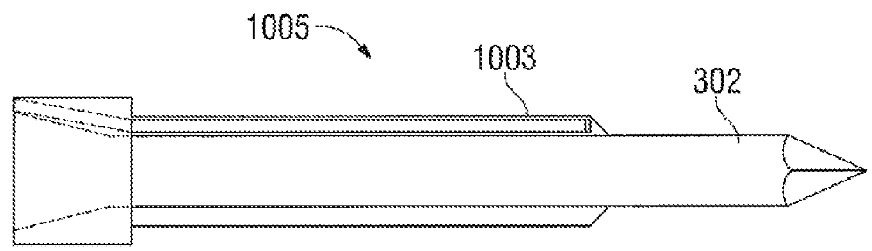
FIG. 10A is a side, cross-sectional view of yet another ablation apparatus provided in accordance with the present disclosure in a straight position.
Figure 10B:
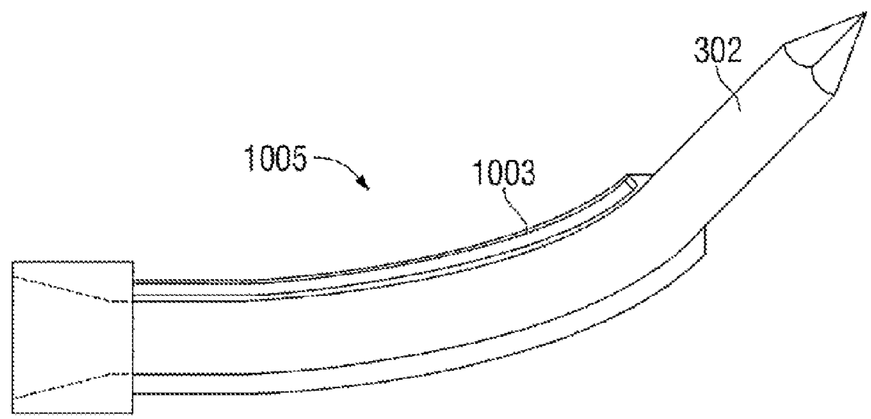
FIG. 10B is a side, cross-sectional view of the ablation apparatus of FIG. 10A in a bent position.
Figure 10C:
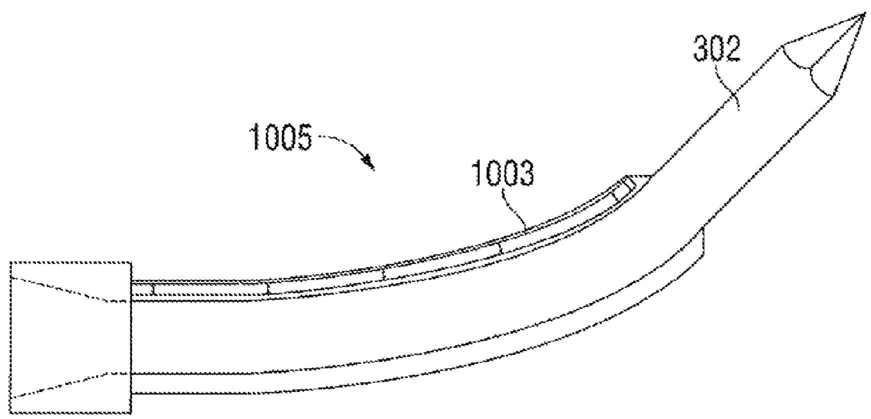
FIG. 10C is a side, cross-sectional view of the ablation apparatus of FIG. 10A in a bent but pressurized rigid position.

Referring to FIGS. 10A-10C, deformation system includes at least one reservoir 1003 disposed within the shaft 1005 and at least one fluid supply (not shown) connected to the reservoir 1003 to act as a pressure source. The shaft 1005 is formed at least partially from a flexible material, similarly as describe above. The shaft 1005 is permitted to be bent when the reservoir 1003 is depressurized, and is inhibited from bending when the reservoir 1003 is pressurized as a result of the pressure within reservoir 1003. Thus, a clinician may bend the shaft 1005 to a desired position when the shaft 1005 is depressurized, and thereafter retain the bent shape of the shaft 1005 by pressurizing the reservoir 1003 while shaft 1005 is bent. Alternatively, the shaft 1005 may be configured to define a pre-determined depressurized shape, e.g., a straight configuration, and a pre-determined pressurized shape, e.g., a bent configuration, such that, upon pressurizing, the shaft 1005 is transitioned from the depressurized shape to the pressurized shape.

Figure 11A:
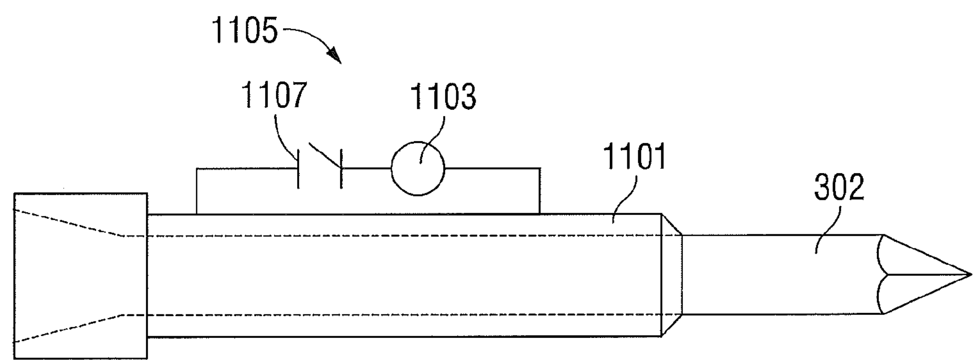
FIG. 11A is a side, cross-sectional view of another ablation apparatus provided in accordance with the present disclosure in a straight, switch-open position.
Figure 11B:
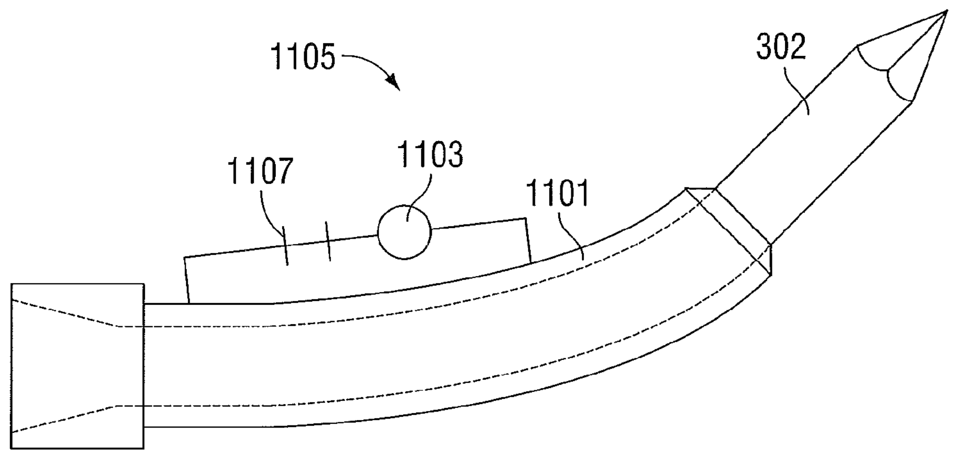
FIG. 11B is a side, cross-sectional view of the ablation apparatus of FIG. 11A in a bent, switch closed position.

Referring to FIGS. 11A and 11B, another embodiment of a deformation system is shown including a shaft 1105 formed at least partially from or including at least one smart material 1101 that has a first physical state when in a first condition and a second physical state when in a second condition.

The first condition may be a neutral condition wherein the at least one smart material 1101 is not subjected to a magnetic or electrical field, or other activator. When shaft 1105 is disposed in the first physical state, corresponding to the neutral first condition, the shaft 1105 may be in a fluidic, viscous, malleable, and/or otherwise deformable state. The first physical state may also be of a substantially rigid state.

The second condition may an activated condition wherein the at least one smart material 1101 is subjected to an activator, e.g., one or more of a magnetic field, electric field, electrical current, or activating chemical. The second physical state caused by the second condition may be a substantially rigid state such that the smart material 1101 resists bending or any other deformation. Where the first physical state is a substantially rigid state, the second physical state is at least one of a fluidic, viscous, malleable, and otherwise deformable state. That is, either the first or second physical state may be the deformable state, with the other being the substantially rigid state.

The at least one smart material 1101 may react to at least one magnetic field such that the magnetic field causes the at least one smart material 1101 to transition from the first physical state to the second physical state. For example, an initially malleable or fluidic smart material 1101 may become substantially rigid when subjected to a magnetic field. In such embodiments, the smart material 1101 may include any ferromagnetic or magneto-rheological composition that is malleable or fluidic when not exposed to a magnetic field. The at least one smart material 1101 may alternatively include a ferrous nano-suspension such as a ferro-fluid that takes a shape when subjected to a magnetic field, or may include a magneto-rheological fluid that increases in apparent viscosity in the presence of a magnetic field. Such fluids may be stored in a reservoir, e.g., a reservoir similar to reservoir 1003 (FIG. 10A). With such magneto-reactive compositions, the at least one smart material 1101 may be subjected to one or more magnetic fields to transition the smart material 1101 from a substantially fluid state to a substantially rigid state.

The at least one smart material 1101 may react to at least one electrical influence (an electrical field and/or electrical current) such that the electrical influence causes the at least one smart material 1101 to transition from a substantially rigid/malleable first physical state to a substantially malleable/rigid second physical state respectively. For example, a smart material 1101 may include a metallic state switching material which includes at least one metal and at least one conductive fluid disposed in pores of the at least one metal. The first physical state of the metallic switching material is a substantially rigid state, and the second physical state is a more malleable state when an electrical influence is applied. The smart material 1101 may include an electro-rheological fluid which is fluidic in the first physical state and transitions to a more viscous or substantially rigid state when an electrical influence is applied thereto, depending on the composition of the electro-rheological fluid and the intensity of the electrical influence. The smart fluid may additionally or alternatively include any suitable shape memory material that can be bent in a first physical state and then returned to a predetermined shaped under the influence of an electrical or thermal influence.

The smart material 1101 may include a chemical mixture that undergoes a hardening cycle at a predetermined time. For example the smart material 1101 may be a liquid in the first physical state that hardens when another chemical is selectively introduced to create a rigid material in the second physical state. The fluid may be stored in a reservoir, e.g., a reservoir similar to reservoir 1003 (FIG. 10A). A non-limiting example of such a chemical mixture is a resin and hardener combination that has a liquid resin in the first physical state that converts to a solid after selective introduction of the hardener into the resin. The hardener may be stored in a separate enclosed cavity in the body such that a clinician may choose when to allow the hardener to mix with the resin, for example, through puncturing the separate enclosed cavity, or through the use of a mechanical floodgate.

In embodiments where the first physical state of the smart material 1101 is a fluidic or malleable state, the clinician may deform the ablation apparatus 100 to be of any desirable state while in the first condition. For example, the clinician may deform the ablation apparatus 100 to fit into a surgical incision more easily, and then deform it again to another desired shape after insertion.

The clinician may then transition the smart material 1101 from the fluidic or malleable first physical state to a substantially rigid second physical state using one or more of the above described systems in order to prevent further deformation of the ablation apparatus 100.

In embodiments where the first physical state of the smart material 1101 is a rigid or substantially rigid state, the clinician may apply any of the above described systems to transition the smart material 1101 from the rigid first physical state to a fluidic or malleable second physical state to deform the ablation apparatus 100 to be of any desirable state while in the second condition. For example, the clinician may deform the ablation apparatus 100 to fit into a surgical incision more easily in the second physical state, and then deform it again to another desired shape after insertion.

The clinician may then transition the smart material 1101 from the fluidic or malleable second physical state back to substantially rigid first physical state by transitioning back to the above described first condition in order to prevent further deformation of the ablation apparatus 100, the at least one port, the first opening, and/or the second opening.

With continued reference to FIGS. 11A and 11B, deformation system, as mentioned above, includes a smart material 1101 formed with, incorporated into, or disposed on or within the shaft 1105. Smart material 1101 is described hereinbelow as being an electro-rheological material 1101 having a rigid state and a deformable state although, as discussed above, various other smart materials 1101 may additionally or alternatively be provided. The smart material 1101 is selectively coupled by at least one switch 1107 to an electrical supply 1103. The electro-rheological material 1101 may be in the deformable state when subjected to an electrical current, e.g. when switch 1107 is closed although the electro-rheological material 1101 may alternatively be in the rigid state when subjected to an electrical current, e.g. when the switch 1107 is closed.

Figure 12A:
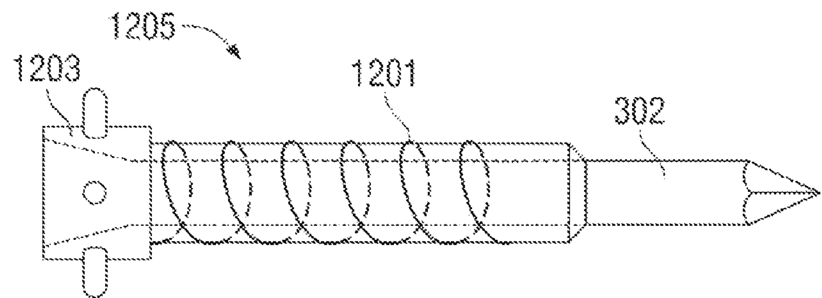
FIG. 12A is a side view of yet another ablation apparatus provided in accordance with the present disclosure in a straight but flexible position.
Figure 12B:
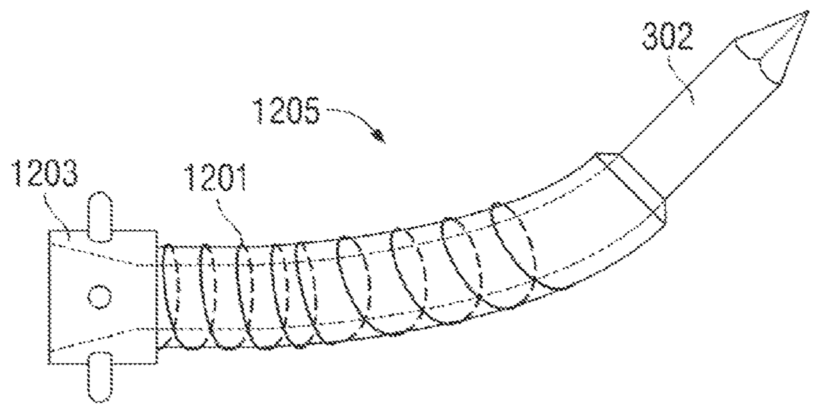
FIG. 12B is a side view of the ablation apparatus of FIG. 12A in a bent but flaccid position.
Figure 12C:
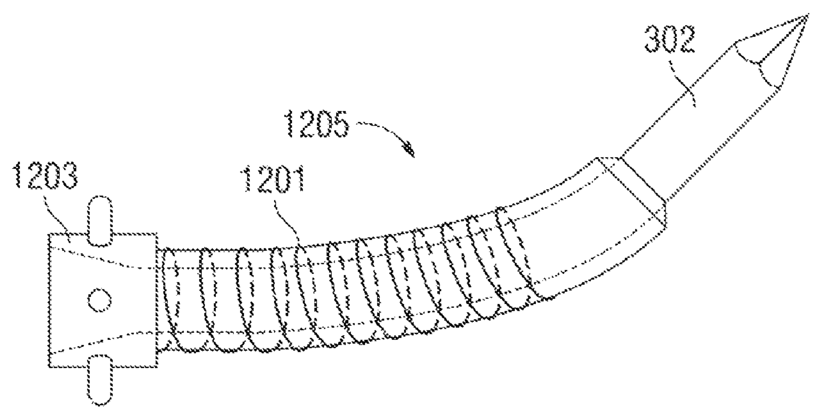
FIG. 12C is a side view of the ablation apparatus of FIG. 12A in bent but tightly-wound rigid position.

Referring to FIGS. 12A-12C, deformation system includes a spring winding 1201 disposed on a shaft 1205. Spring winding 1201 is connected to a tightener 1203 such that the spring winding 1203 may be tightened to become substantially rigid and loosened to become deformable. Spring winding 1201 may be fixed at both ends, one end on the shaft 1205 and the other end to the tightener 1203. For example, the shaft 1205 may be bent while the spring winding 1201 is loose as in FIG. 12B. The spring winding 1201 may be tightened after bending to hold shape as shown in FIG. 12C.

A method for ablating a target site is further disclosed and includes providing an ablation apparatus including a proximal body portion, a shaft extending distally from the proximal body portion, the shaft being selectively deformable utilizing at least one deformation system as described above to allow the shaft to be bent, and at least one electrode disposed at least partially within the shaft and extending from a distal end of the shaft. The method may further include inserting the shaft into an incision and bending the shaft to position the at least one electrode at a target location, and ablating the target location.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing FIGS. are presented only to demonstrate certain examples of the disclosure. Other elements, steps, methods, and techniques that are insubstantially different from those described above and/or in the appended claims are also intended to be within the scope of the disclosure.

What is claimed is:

1. An ablation apparatus, comprising:

a proximal body portion;

a shaft extending distally from the proximal body portion, the shaft selectively deformable utilizing at least one deformation system between a first position wherein the shaft is substantially straight and a second position wherein the shaft is bent, the at least one deformation system configured to retain the shaft in each of the first and second positions and including at least two links operably coupled to each other, each link of the at least two links defining:

a flange on a first end portion, the flange defining a socket therein, the socket defining an uninterrupted inner surface about a circumference thereof; and a hinge portion on a second, opposite end portion, the hinge portion defining a cylindrical profile and defining a cavity therein having an arcuate profile extending along a longitudinal axis thereof, wherein the socket of the flange portion of one of the at least two links is configured to rotatably receive the hinge portion of another one of the at least two links; and at least one electrode disposed within the shaft and extending distally therefrom, the at least one electrode being in mechanical communication with the shaft such that deformation of the shaft causes a corresponding deformation of the at least one electrode, the at least one electrode defining a pointed distal tip configured to pierce tissue, the pointed distal tip being maintained distal of the shaft during deformation of the shaft.

2. The ablation apparatus of claim 1, wherein the deformation system comprises a goose-neck type shaft.

3. The ablation apparatus of claim 2, wherein the goose-neck type shaft includes a flexible layer disposed thereon to cover one or more separations between the at least two links.

4. The ablation apparatus of claim 1, wherein the shaft is made of a flexible material, and the deformation system comprises a line pull system, the line pull system comprising:

at least one anchor fixedly attached to the shaft; and at least one line connected to the at least one anchor and configured to be pulled to bend the shaft.

5. The ablation apparatus of claim 4, wherein the at least one line pull system comprises a first anchor connected to a first line, a second anchor connected to a second line and a third anchor connected to a third line, each anchor being spaced about equal distances circumferentially around the shaft such that the shaft is bendable in any desired direction.

6. The ablation apparatus of claim 1, wherein the shaft further comprises a flexible material and the deformation system comprises at least one of a material selected from the group consisting of a magnet and a ferromagnetic material, the material allowing the shaft to be moved by a magnetic field in the direction of the magnetic field.

7. The ablation apparatus of claim 6, wherein the deformation system further includes the material disposed within the flexible material at the distal end of the shaft.

8. The ablation apparatus of claim 1, wherein the deformation system comprises a weave having a rigid state and a deformable state.

9. The ablation apparatus of claim 8, wherein the rigid state is an elongated state and the deformable state is a neutral state.

10. The ablation apparatus of claim 8, wherein the deformable state is an elongated state and the rigid state is a neutral state.

11. The ablation apparatus of claim 1, wherein the deformation system comprises at least one semi-rigid rod configured to bend and hold the bent position.

12. The ablation apparatus of claim 1, wherein the deformation system comprises:

at least one reservoir disposed within the shaft; and at least one fluid supply connected to the reservoir to act as a pressure source, wherein the shaft is bendable when the reservoir is depressurized and rigid when the reservoir is pressurized.

13. The ablation apparatus of claim 1, wherein the deformation system comprises an electro-rheological material selectively connected to an electrical supply, the electro-rheological material having a rigid state and a deformable state.

14. The ablation apparatus of claim 13, wherein the electro-rheological material is in the deformable state when subjected to an electrical current.

15. The ablation apparatus of claim 13, wherein the electro-rheological material is in the rigid state when subjected to an electrical current.

16. The ablation apparatus of claim 1, wherein the deformation system comprises a magneto-rheological material selectively subjected to a magnetic field, the magneto-rheological material having a rigid state and a deformable state.

17. The ablation apparatus of claim 16, wherein the magneto-rheological material is in the rigid state when subjected to a magnetic field.

18. The ablation apparatus of claim 1, wherein the deformation system comprises a spring winding disposed on said shaft, wherein the spring winding is connected to a tightener such that spring winding may be tightened to become substantially rigid and loosened to become deformable.

19. The ablation apparatus of claim 1, wherein the socket of each flange of the at least two links defines an arcuate profile extending along the longitudinal axis disposed in juxtaposed relation to the arcuate profile.

20. The ablation apparatus of claim 19, wherein an intersection of the arcuate profile of the cavity and the arcuate profile defined by the socket define an aperture having an inner dimension that is less than the inner dimension of each of the arcuate profile of the cavity and the arcuate profile defined by the socket.

* * * * *

UNITED STATES PATENT AND TRADEMARK OFFICE

CERTIFICATE OF CORRECTION

PATENT NO. : 9,993,283 B2
APPLICATION NO. : 14/035451
DATED : June 12, 2018
INVENTOR(S) : Casey M. Ladtkow It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 364 days.

Signed and Sealed this
Twenty-fifth Day of June, 2019

Andrei Iancu
*Director of the United States Patent and Trademark Office*